(12) United States Patent
Hamilton (10) Patent No.: US 12,011,442 B2
(45) Date of Patent: Jun. 18, 2024

(54) SOLID-STATE FORMS OF ABEMACICLIB, THEIR USE AND PREPARATION

(71) Applicant: MACFARLAN SMITH LIMITED, Edinburgh (GB)

(72) Inventor: Clifton R. Hamilton, Devens, MA (US)

(73) Assignee: Macfarlan Smith Limited, Edinburgh (GB)

(*) Notice: Subject to any disclaimer, the term of this patent is extended or adjusted under 35 U.S.C. 154(b) by 0 days.

(21) Appl. No.: 16/948,893

(22) Filed: Oct. 5, 2020

(65) Prior Publication Data

US 2021/0015817 A1    Jan. 21, 2021

Related U.S. Application Data

(63) Continuation of application No. PCT/US2019/025819, filed on Apr. 4, 2019.

(60) Provisional application No. 62/653,273, filed on Apr. 5, 2018.

(51) Int. Cl.
  *C07D 401/14*     (2006.01)
  *A61K 31/506*     (2006.01)

(52) U.S. Cl.
  CPC ........ *A61K 31/506* (2013.01); *C07B 2200/13* (2013.01)

(58) Field of Classification Search
  CPC ........................... C07D 401/14; A61K 31/506

USPC .......................................... 544/295; 514/275
  See application file for complete search history.

(56) References Cited

U.S. PATENT DOCUMENTS

| 7,855,211 B2 | 12/2010 | Coates et al. |
| 9,969,718 B2 | 5/2018 | Xu |
| 2017/0173013 A1 | 6/2017 | Chan |

FOREIGN PATENT DOCUMENTS

| CN | 107868082 A | 4/2018 |
| CN | 109761959 A | 5/2019 |
| WO | 2017108781 A1 | 6/2017 |
| WO | 2017211268 A1 | 12/2017 |
| WO | 2019102492 A1 | 5/2019 |
| WO | 2019200502 A1 | 10/2019 |

OTHER PUBLICATIONS

Caira, "Crystalline Polymorphism of Organic Compounds", Topics in Current Chemistry, Springer, Berlin, DE, Jan. 1, 1998, vol. 198, pp. 163-208.

*Primary Examiner* — Jeffrey H Murray (57) ABSTRACT

The invention relates to a crystalline methanol solvate or hydrate form of ABC, and an anhydrous form of ABC, that reversibly forms a hydrate of ABC. The invention is also directed to the preparation of the aforesaid solvate, hydrate, and anhydrous solid-state forms of ABC. Furthermore, the invention relates to pharmaceutical compositions comprising at least one of the aforesaid crystalline forms of ABC according to the invention, and the pharmaceutical use of at least one of the aforesaid crystalline forms of ABC according to the invention for treatment of a patient in need thereof.

5 Claims, 9 Drawing Sheets

SOLID-STATE FORMS OF ABEMACICLIB, THEIR USE AND PREPARATION

CROSS-REFERENCE TO RELATED APPLICATIONS

This application is a continuation of International Application No. PCT/US2019/025819, filed Apr. 4, 2019, which claims priority to U.S. Provisional Patent Application No. 62/653,273, Apr. 5, 2018, the disclosures of which are incorporated herein by reference in their entireties for all purposes.

FIELD OF THE INVENTION

The invention relates to a solid-state methanol solvate, hydrate, and anhydrous forms of Abemaciclib (ABC), the preparation of the aforesaid forms and their use.

BACKGROUND OF THE INVENTION

ABC, N-[5-[(4-Ethyl-1-piperazinyl)methyl]-2-pyridinyl]-5-fluoro-4-[4-fluoro-2-methyl-1-(1-methylethyl)-1H-benzimidazol-6-yl]-2-pyrimidinamine, of the formula I below, is an

I

CDK inhibitor selective for CDK4 and CDK6 that is useful for the treatment of advanced or metastatic breast cancers.

U.S. Pat. No. 7,855,211 and US Patent Application 20170173013 disclose the preparation of ABC and two polymorphs Form I and III. Form I has XRPD peaks 4.51, 5.89, 8.98, 11.2, 12.57, 13.09, 15.93, 16.31, 17.01, 18.58, 18.82, 20.86, 21.9, 23.12, 23.53, 26.71 and 26.85±0.2° 2⊖. Form III has XRPD peaks 7.44, 10.91, 11.54, 12.13, 13.89, 14.91, 15.63, 16.06, 18.59, 18.94, 20.43, 21.29, 21.91, 22.13, 22.45, 23.12, 23.42, 25.95, and 29.42. WO2017108781 discloses Form IV of ABC can be characterized by XRPD peak(s) at 6.0, 6.8, 7.5, 10.4, 12.0, 13.4, 13.9, 15.3, 15.6, 16.3, 18.2, 18.5, 19.2, 19.9, 21.0, 22.2, 22.7, 25.0, 26.1, 27.1, 28.2 and 31.7±0.2° ⊖. Form IV of ABC is disclosed as having one endotherm with an onset temperature of 123° C. (±5°) and a peak temperature of 133° C. (±1°), other endotherms with an onset temperature of 174° C. (+2°) and 181° C. (+2°) as well as peak temperatures of 176° C. (±1°) and 182° C. (±1°), respectively and an exotherm with an onset temperature of 137° C. (±5°) and a peak temperature of 140° C. (±2°).

None of the references disclose a solid-state MeOH solvate or hydrate of ABC. None of the references discloses an anhydrous polymorph of ABC, that reversibly forms a water solvated form of ABC.

SUMMARY OF THE INVENTION

The invention relates to a crystalline methanol solvate or hydrate form of ABC, and an anhydrous form of ABC, that reversibly forms a hydrate of ABC. The invention is also directed to the preparation of the aforesaid solvate, hydrate, and anhydrous solid-state forms of ABC. Furthermore, the invention relates to pharmaceutical compositions comprising at least one of the aforesaid crystalline forms of ABC according to the invention, and the pharmaceutical use of at least one of the aforesaid crystalline forms of ABC according to the invention for treatment of a patient in need thereof.

DETAILED DESCRIPTION OF THE INVENTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are not intended to be limited to the examples described herein and shown, but are to be accorded the scope consistent with the claims.

The term "solid-state form" of ABC, as used herein, includes crystalline or polymorphic forms, amorphous phases, and solvates.

The use of the term "about" or the symbol "~" includes and describes the value or parameter per se. For example, "about x" includes and describes "x" per se. The term "about" when used in association with a measurement, or used to modify a value, a unit, a constant, or a range of values, refers to variations of +/−5 percent.

The term "substantially" or "substantially free/pure" with respect to a solid-state form means that the form contains about less than 30 percent, about less than 20 percent, about less than 15 percent, about less than 10 percent, about less than 5 percent, or about less than 1 percent by weight of impurities. Impurities may, for example, include other polymorphic forms, water and solvents other than that in the crystalline solid-state form.

The term "room temperature" is defined as a temperature between 15-29° C.; preferably between 20-23° C.

The term "to dry/drying/dried", as used in this patent application, means to dry/drying/dried at 45° C. and under vacuum.

All ranges recited herein include the endpoints. Terms such as "about", "generally", and "substantially," are to be construed as modifying a term or value such that it is not an absolute. This includes, at very least, the degree of expected experimental error, technique error and instrument error for a given technique used to measure a value.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

Embodiments

It is therefore an object of the present invention to provide solid-state MeOH solvate or hydrate form of ABC, and a solid-state anhydrous polymorph of ABC, that reversibly forms a hydrate form of ABC. It is further an object of the present invention to provide a process for the preparation of such MeOH solvate or hydrate form of ABC and anhydrous polymorph of ABC, that reversibly forms a hydrate form of ABC, further particularly prepared from a MeOH solvate form of ABC. It is a yet another object of the invention to use a MeOH solvate or hydrate form of ABC, or anhydrous polymorph of ABC, that reversibly forms a hydrate form of ABC, further particularly prepared from a MeOH solvate form of ABC, to prepare a pharmaceutical dosage form of ABC.

ABC is dissolved in warm (about 50-60° C. range, preferred about 55° C.) methanol (about 200 mg/mL) and then cooling (−10° C.-−5° C. range, preferred −5° C.) to force precipitation of a white powder, which is Form I of the variable methanol solvate of ABC.

Form I of the variable methanol solvate of ABC is vacuum dried at an elevated temperature (40-60° C. range, preferred 45° C.) for 8 hours or more to yield Form II of the anhydrous of ABC.

Form II of the anhydrous of ABC is placed in a humid environment (about >60% RH, preferably 80% RH at temperatures between about 15-40° C., preferably about 25° C.) to yield Form III of hydrate of ABC.

In another general aspect, is the use of a solid-state form of ABC according to the invention for use in preparing a pharmaceutical composition; more particularly where the composition is a solution together with one or more pharmaceutically acceptable ingredients. Pharmaceutical compositions comprising a solid-state form of ABC according to the invention may be prepared according to WO2017108781, which is incorporated herein by reference in its entirety; more particularly the composition could comprise microcrystalline cellulose 102, microcrystalline cellulose 101, lactose monohydrate, croscarmellose sodium, sodium stearyl fumarate, silicon dioxide. The dosage of the pharmaceutical compositions may be varied over a wide range. Optimal dosages and dosage regimens to be administered may be readily determined by those skilled in the art, and will vary with the mode of administration, the strength of the preparation and the advancement of the disease condition. In addition, factors associated with the patient being treated, including patient's sex, age, weight, diet, physical activity, time of administration and concomitant diseases, will result in the need to adjust dosages and/or regimens. For example, a total dosage of the pharmaceutical composition of the invention would be available as 300 mg or 400 mg (150 mg or 200 mg twice daily), using dosages of 50 mg, 100 mg, 150 mg, and 200 mg tablets. Furthermore, the present invention also relates to a method for treating (1) in combination with an aromatase inhibitor as initial endocrine-based therapy for the treatment of postmenopausal women with hormone receptor (HR)-positive, human epidermal growth factor receptor 2 (HER2)-negative advanced or metastatic breast cancer; (2) in combination with fulvestrant for the treatment of women with hormone receptor (HR)-positive, human epidermal growth factor receptor 2 (HER2)-negative advanced or metastatic breast cancer with disease progression following endocrine therapy; and (3) as monotherapy for the treatment of adult patients with HR-positive, HER2-negative advanced or metastatic breast cancer with disease progression following endocrine therapy and prior chemotherapy in the metastatic setting.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present invention and the invention is not intended to be limited to the examples described herein and shown.

Examples

Analytical Experimental
Analysis—XRPD (X-Ray Powder Diffractometry)
Diffractograms are obtained with laboratory diffractometer, BRUKER D-8 Advance diffractometer, using radiation CuKα (X=1.542 A), and Lynxeye super speed detector.

Relative intensities for peak values can vary depending on several factors, including sample preparation, mounting, and analytical procedure and settings of the instrument that is used to obtain the spectrum.

SCXRD (Single Crystal X-Ray Diffraction) is obtained using either PILATUS3 X CdTe 1M detector at Beamline 15-ID-B of ChemMatCARS or Bruker D8 Venture PHOTON 100 CMOS diffractometer equipped with a CuKα INCOATEC Imus micro-focus source ($\lambda$=1.54178 Å).

Analysis—DSC (Differential Scanning calorimetry)
DSC measurements are performed on a calorimeter, TA Instruments Q2000 and RSC40.

The sample are weighed in aluminum pans. Investigations were performed in a temperature range of 20-400° C. with a heating rate of 10° C./min, purging with nitrogen at a flow rate of 50 mL/min.

Analysis—TGA (Thermo Gravimetric Analysis)

TGA measurements are recorded using TA Q500 instrument. The samples are weighed in aluminum pans. TGA investigations are performed at a heating rate of 10.0° C./min over a temperature range of 30-350° C., purging with nitrogen at a flow rate of 60 mL/min.

Analysis—$^1$H NMR $^1$H NMR measurements are recorded using Bruker 300 MHz Advance NMR spectrometer in DMSO-d6.

Analysis—Polarized Light Microscopy (PLM)

Samples are analyzed using an Olympus BX53 polarized light microscope equipped with a PAXcam 3 digital microscope camera.

I. Solid-State Form I of Variable Methanol Solvate of ABC

Figure 1:
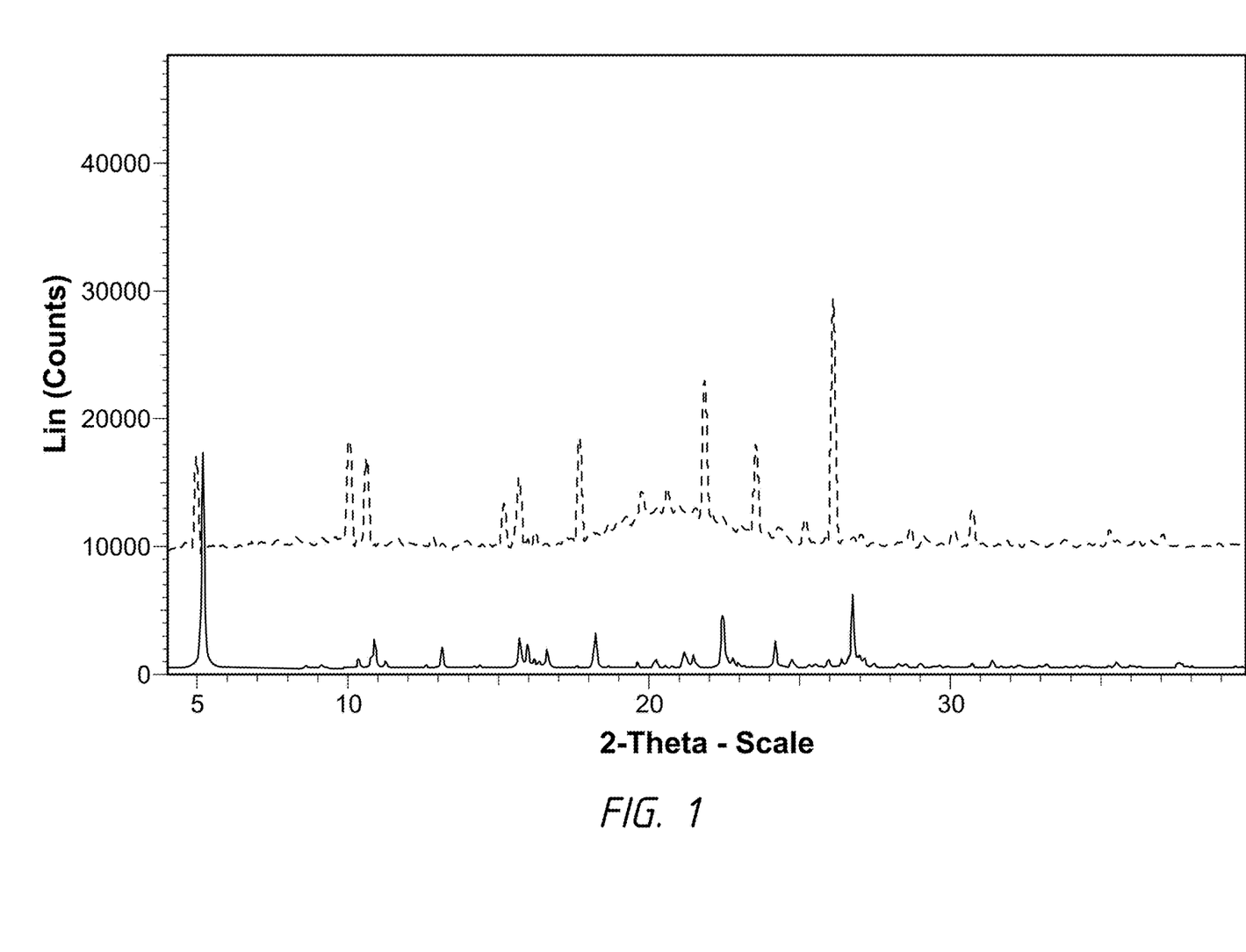
FIG. 1 is an XRPD pattern of solid-state Form I of partially desolvated variable methanol solvate of ABC (top dash line plot) and calculated pattern from SCXRD data for Form I of variable methanol solvate of ABC (bottom solid line plot).
Figure 2:
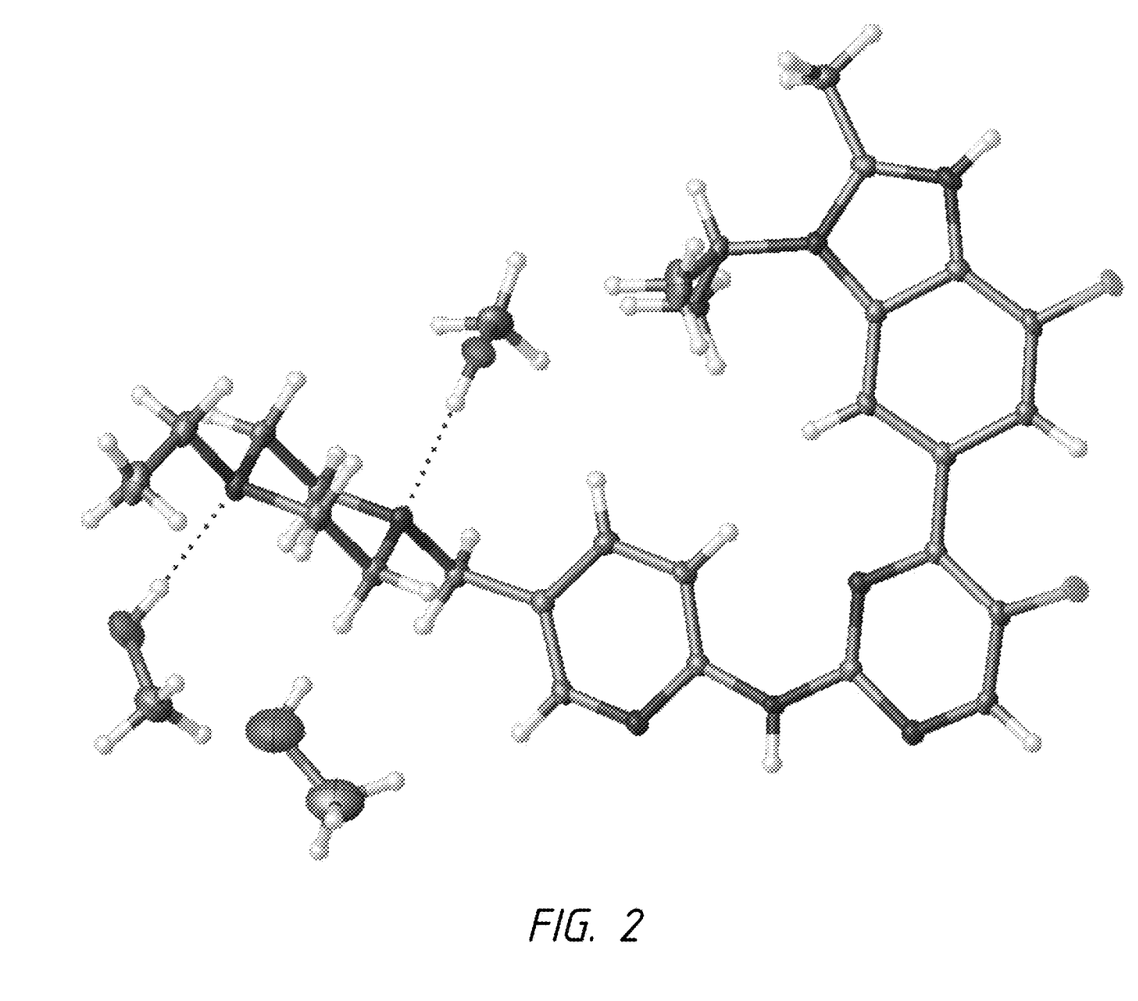
FIG. 2 is a three-dimensional structure of crystalline Form I of variable methanol solvate of ABC that is discerned from SCXRD.

A variable methanol solvate of ABC is produced by dissolving ABC in warm (55° C.) methanol (about 200 mg/mL) and then cooling (−5° C.) to force precipitation of a white powder. The resulting powder is examined by XRPD while still wet (FIG. 1, top pattern). Single crystals are grown by slow evaporation of methanol into an antisolvent (preferably ethyl acetate) or by slowly cooling a saturated solution from 50° C. to 0° C. over the course of several hours, and not exposed to air, to obviate evaporation of the solvate and the collapse of the crystalline lattice. Single crystal X-ray diffraction (SCXRD) data is undertaken at 100° K to improve diffraction quality as well as prevent desolvation. The calculated XRPD pattern for the single crystal (FIG. 1, bottom pattern) did not perfectly match the XRPD pattern of the wet crystal because the conditions under which the SCXRD is collected results in small changes in the unit cell that results in shifts in the calculated XRPD peaks for the variable methanol solvate of ABC. The single crystal is determined to be Form I of variable methanol solvate of ABC (FIG. 2) having about 2.5-3 molecules of methanol, preferably about 2.75 molecules of methanol. Form I of variable methanol solvate of ABC is unstable.

The XRPD is directed to the solid-state Form I of variable methanol solvate of ABC, and 2Θ, and relative % intensity values for peaks are shown in Table I.

TABLE I

| Angle 2Θ ° | Intensity % % |
|---|---|
| 4.9 | 39.7 |
| 10.0 | 42.7 |
| 10.6 | 34.8 |
| 15.7 | 27.8 |
| 17.7 | 42.1 |
| 21.8 | 58.8 |
| 23.6 | 36.8 |
| 26.1 | 100 |

The angle measurements are ±0.2° 2Θ. Key defining peaks for solid-state Form I of variable methanol solvate of ABC include 10.0, 17.7, 21.8 and 26.1° 2Θ.

Figure 3:
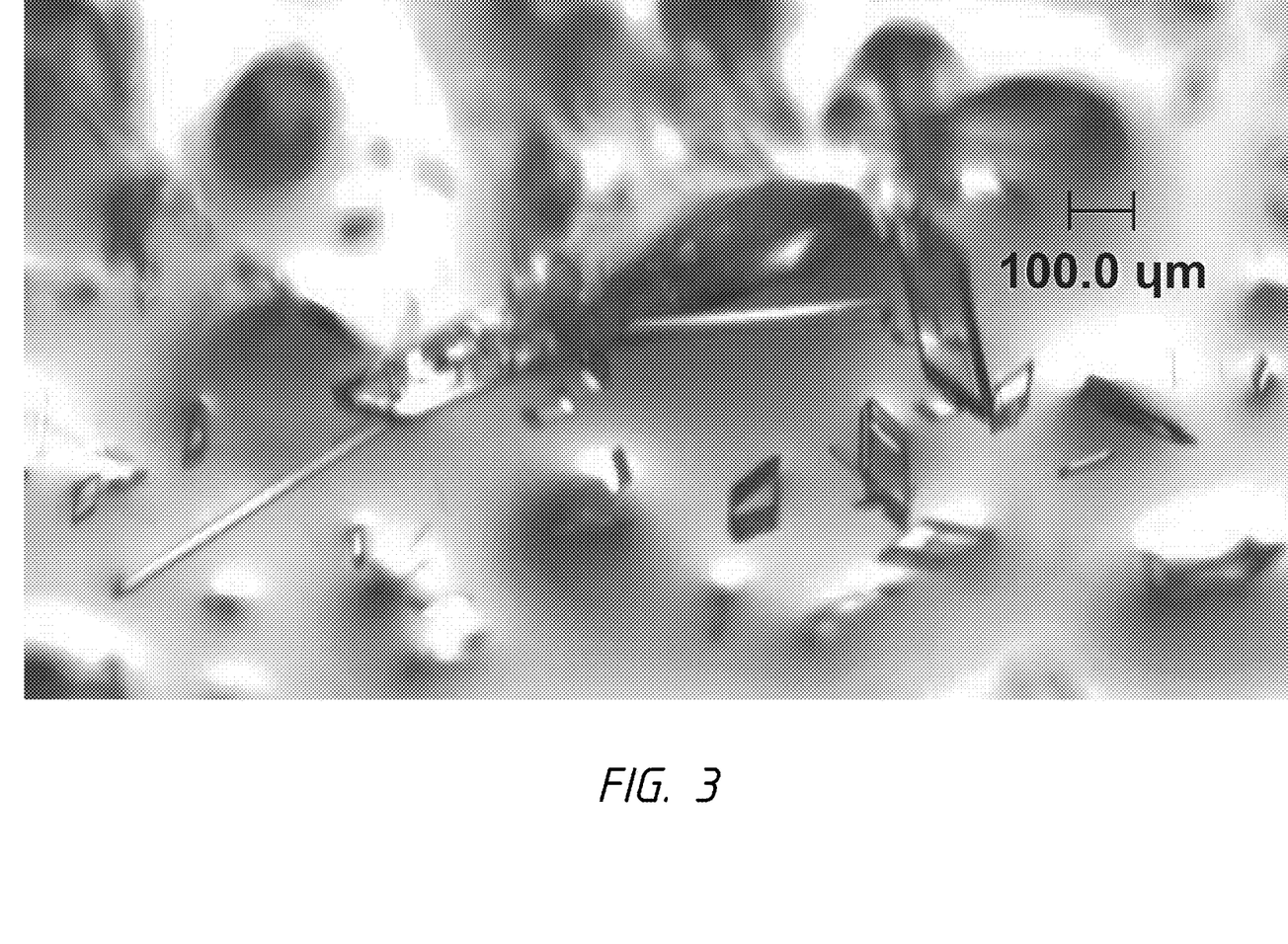
FIG. 3 is PLM of crystals of solid-state Form I of variable methanol solvate of ABC.

Single crystal parameters for the solid-state Form I of variable methanol solvated ABC as determined by SCXRD are:

a=8.3338(4) Å
b=10.5427(5) Å
c=17.6133(10) Å
α=100.953(2)°
β=97.285(2)°
γ=93.819(2)°
Cell Volume=1500.51(13) Å$^3$ Crystals of the Form I of the variable methanol solvate of ABC are examined by PLM (FIG. 3) and determined to be rhomboid.

Figure 4:
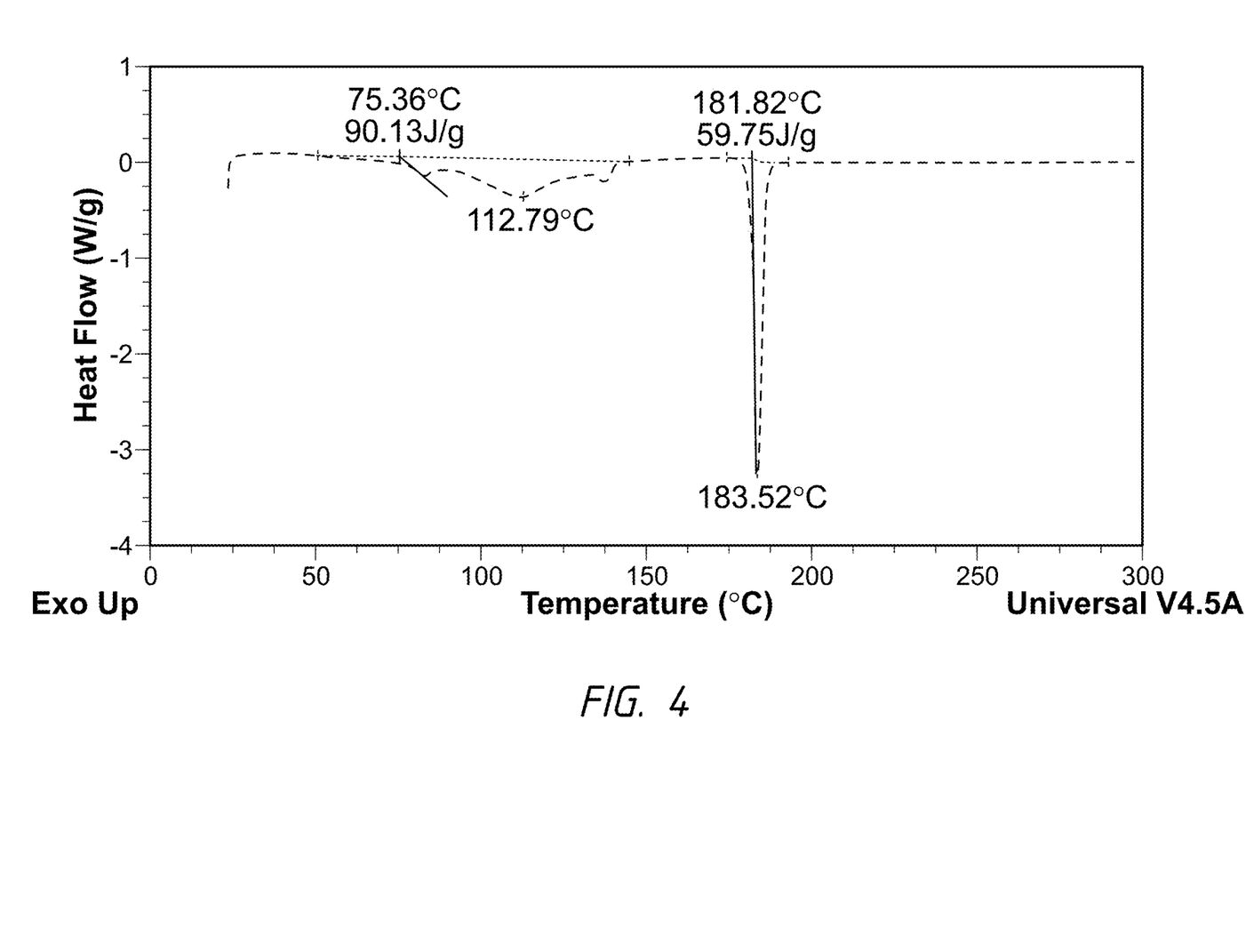
FIG. 4 is DSC plot of solid-state Form I of variable methanol solvate of ABC.

The DSC plot (FIG. 4) for the Form I of the variable methanol solvate of ABC shows ill-defined endotherms related to solvent and a melt of about 184° C.

II. Solid-State Form II of Anhydrous ABC

Solid-state Form II of anhydrous ABC is prepared by vacuum drying Form I of the variable methanol solvate of ABC at an elevated temperature (45° C.) for about 8 hours or more.

The XRPD represents the solid-state Form II of anhydrous ABC (FIG. 5, middle pattern) yielded from solid-state Form I of variable methanol solvate ABC (FIG. 5, bottom pattern), and 2Θ, and relative % intensity values for peaks are shown in Table II.

TABLE II

| Angle 2Θ ° | Intensity % % |
|---|---|
| 5.1 | 100 |
| 6.2 | 30.6 |
| 10.3 | 28.9 |
| 16.8 | 38 |
| 22.8 | 16.3 |
| 24.5 | 16.9 |

The angle measurements are ±0.2° 2Θ. Key defining peaks for solid-state Form II anhydrous ABC include 5.1, 6.2 and 16.8° 2Θ.

Figure 6:
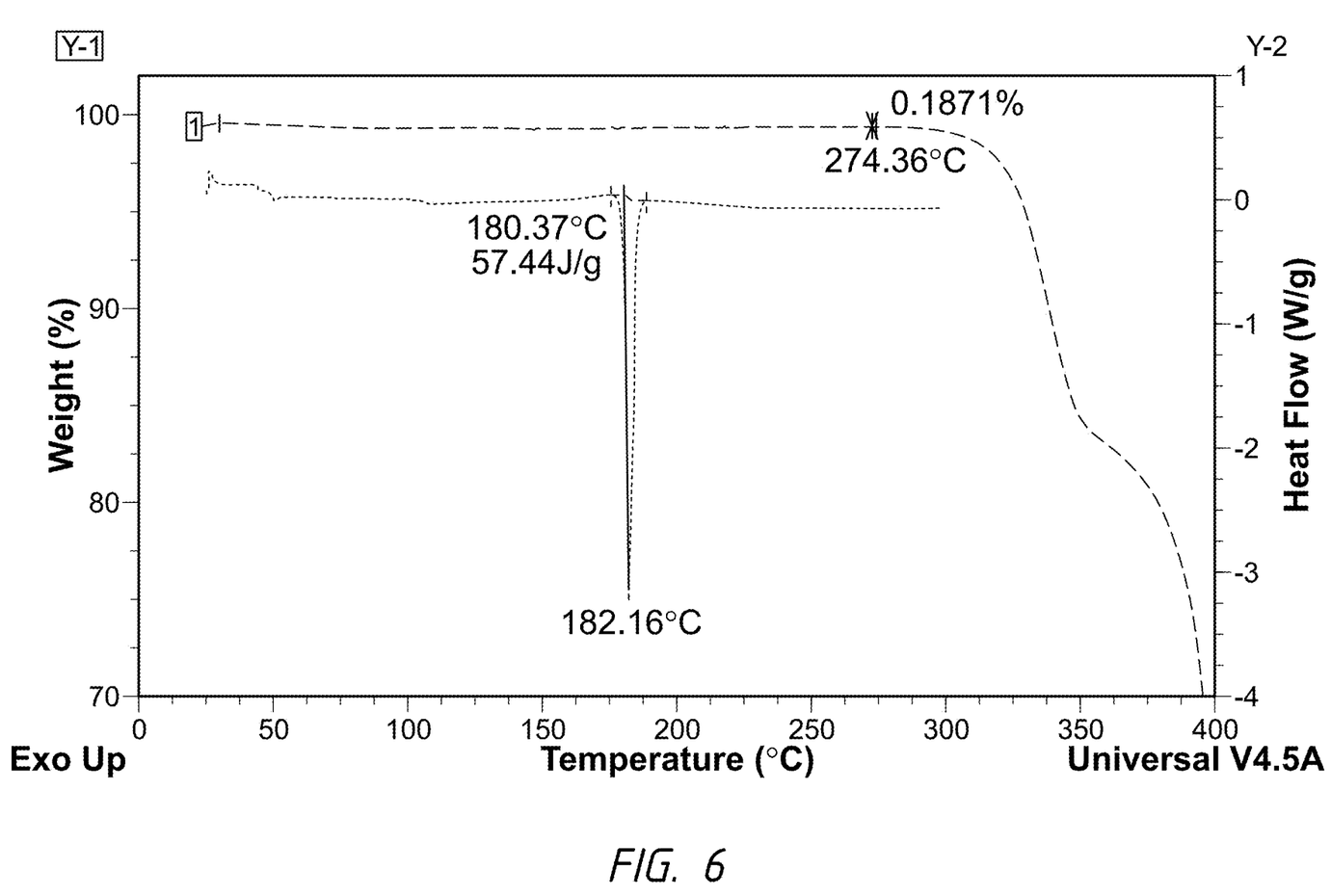
FIG. 6 is directed to DSC and TGA plots of solid-state Form II of anhydrous ABC.
Figure 7:
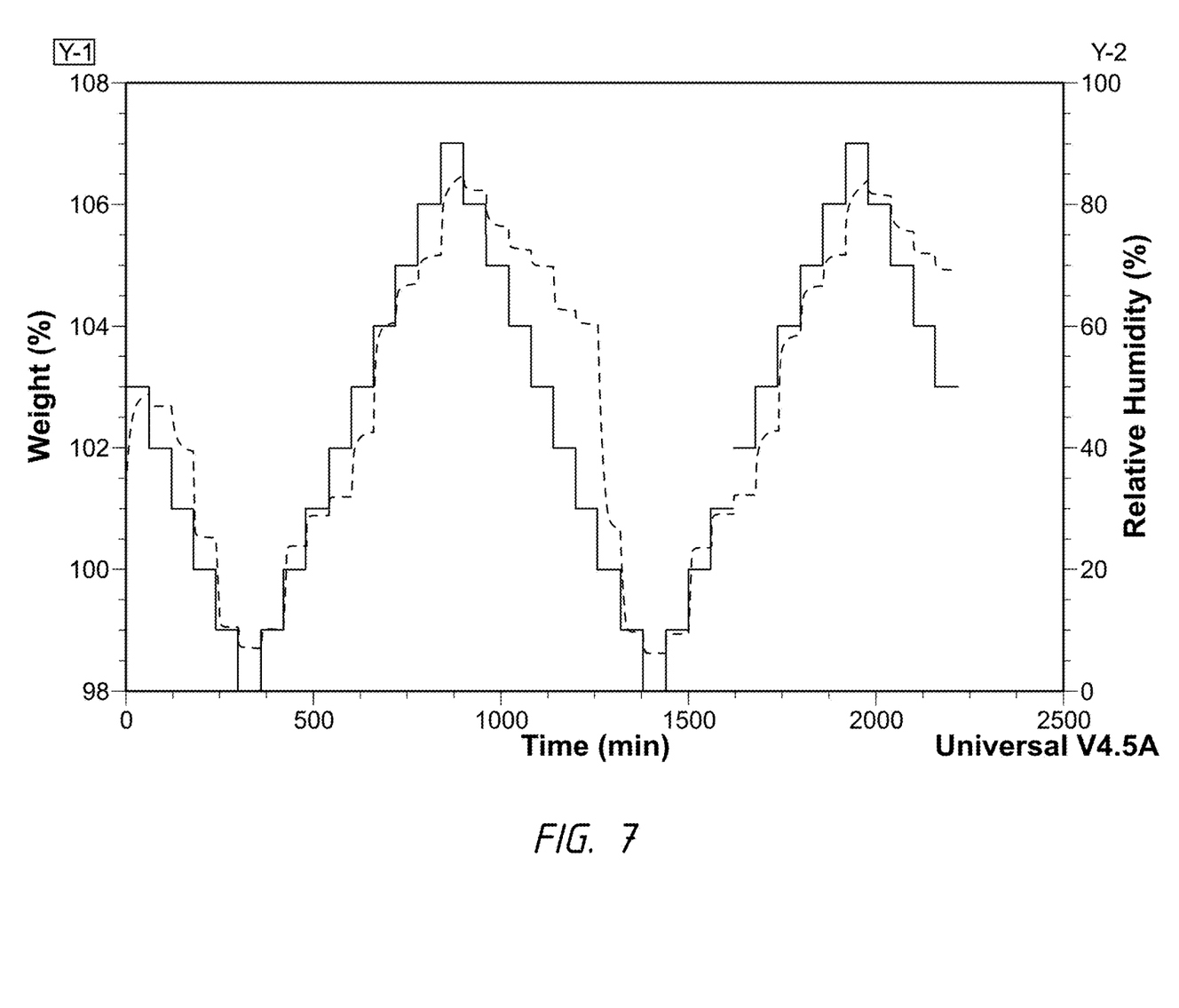
FIG. 7 is dynamic vapor sorption (DVS) plot of solid-state of Form II of anhydrous ABC.
Figure 8:
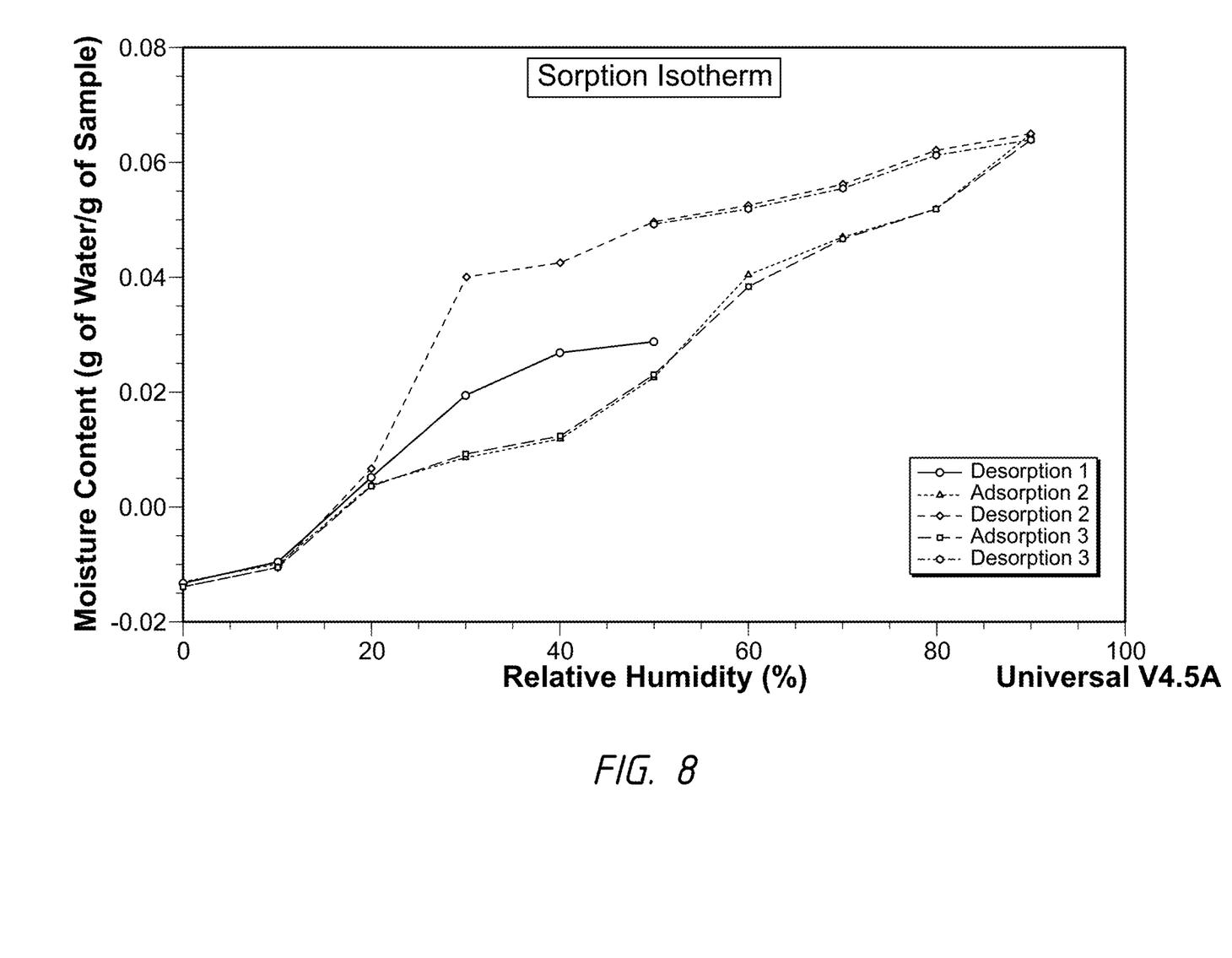
FIG. 8 is sorption isotherm plot of solid-state of Form II of anhydrous ABC.

The DSC plot (FIG. 6) for the solid-state Form II anhydrous ABC melts from 180° C. to 182° C., and the TGA plot shows the onset of decomposition to be at about 320° C. (FIG. 6). The DVS plot (FIG. 7) of solid-state Form II anhydrous ABC absorbs about 8% $H_2O$ by weight between 0-90% relative humidity (RH). The sorption isotherm plot of solid-state Form II anhydrous ABC indicates that the water adsorption is largely linear, while the desorption occurs primarily between 30-20% RH, where 4% $H_2O$ in lost at this one step (FIG. 8).

III. Solid-State Form III of Hydrate of ABC

Solid-state Form III of hydrate solvate of ABC is produced by storing several hundred mg of Form II of anhydrous ABC at 40 C/75% RH or 25 C/97% RH for 1 week. The results in Figures VII and VIII show that the transformation from Form II anhydrous ABC to Form III of hydrate of ABC is reversible, with the large drop in weight during desorption at 20% RH of about 4%, which is consistent with the loss of a molecule of water.

Figure 5:
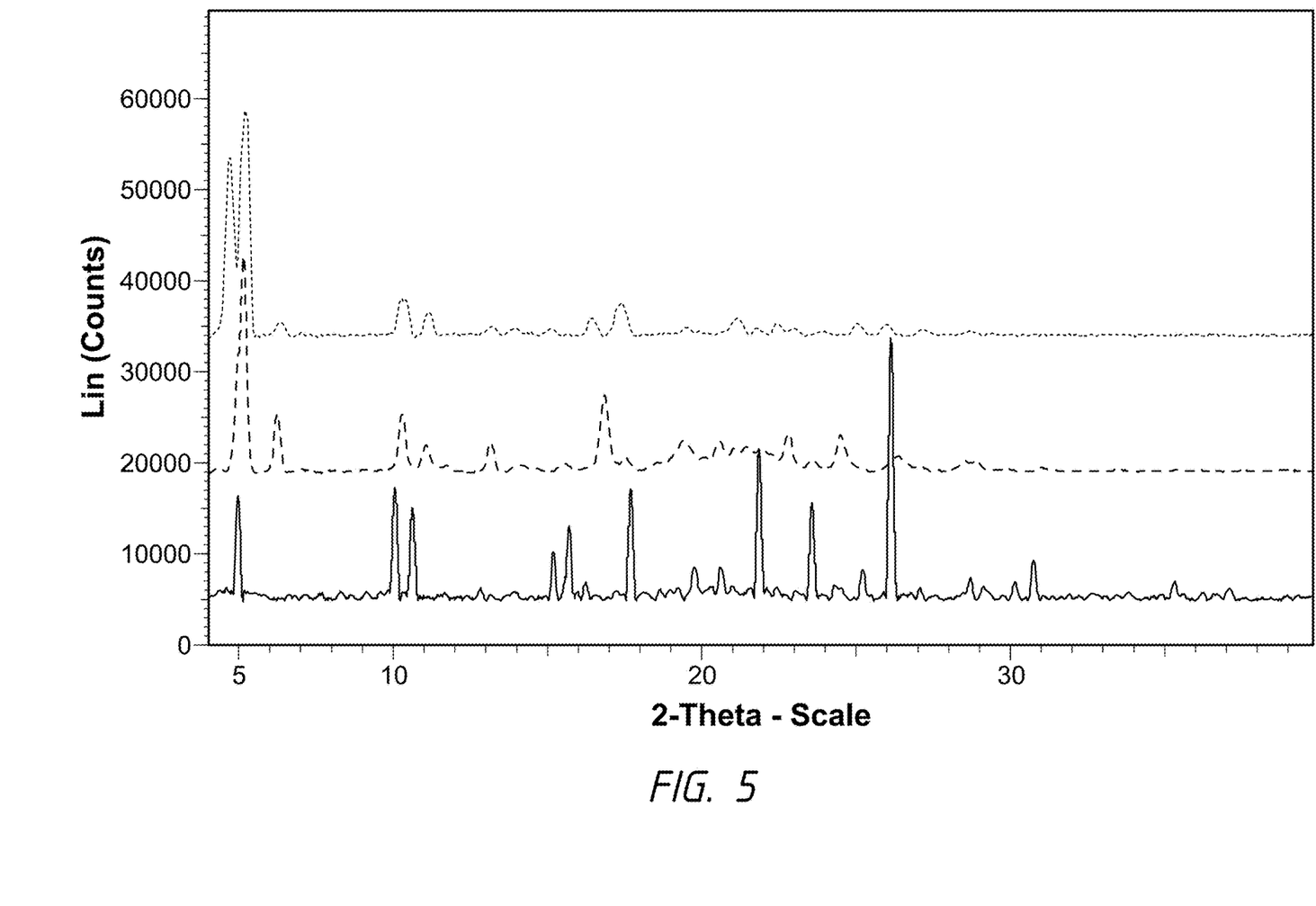
FIG. 5 is comparisons of XRPD patterns of solid-state Form I of variable methanol solvate of ABC (bottom plot), Form II of anhydrous ABC (middle plot) and Form III of hydrate of ABC (top plot).

The XRPD of the solid-state Form III of hydrate of ABC is represented in FIG. 5 (top pattern) and is obtained from the solid state Form II of anhydrous ABC (FIG. 5, middle pattern). 2Θ, and relative % intensity values for peaks for solid-state Form III of hydrate of ABC are shown in Table III.

TABLE III

| Angle 2Θ ° | Intensity % % |
|---|---|
| 4.7 | 78.6 |
| 5.2 | 100 |
| 6.3 | 5.9 |
| 10.3 | 15.1 |
| 11.1 | 10.1 |
| 16.4 | 7.4 |

TABLE III-continued

| Angle 2Θ ° | Intensity % |
|---|---|
| 17.4 | 14.1 |
| 21.1 | 7.3 |
| 22.4 | 5 |
| 25.1 | 4.9 |
| 26.0 | 4.1 |

The angle measurements are ±0.2° 2Θ. Key defining peaks for solid-state Form III of hydrate of ABC include a peak at about 5.2°, but also has a new peak at 4.7° 2Θ.

Figure 9:
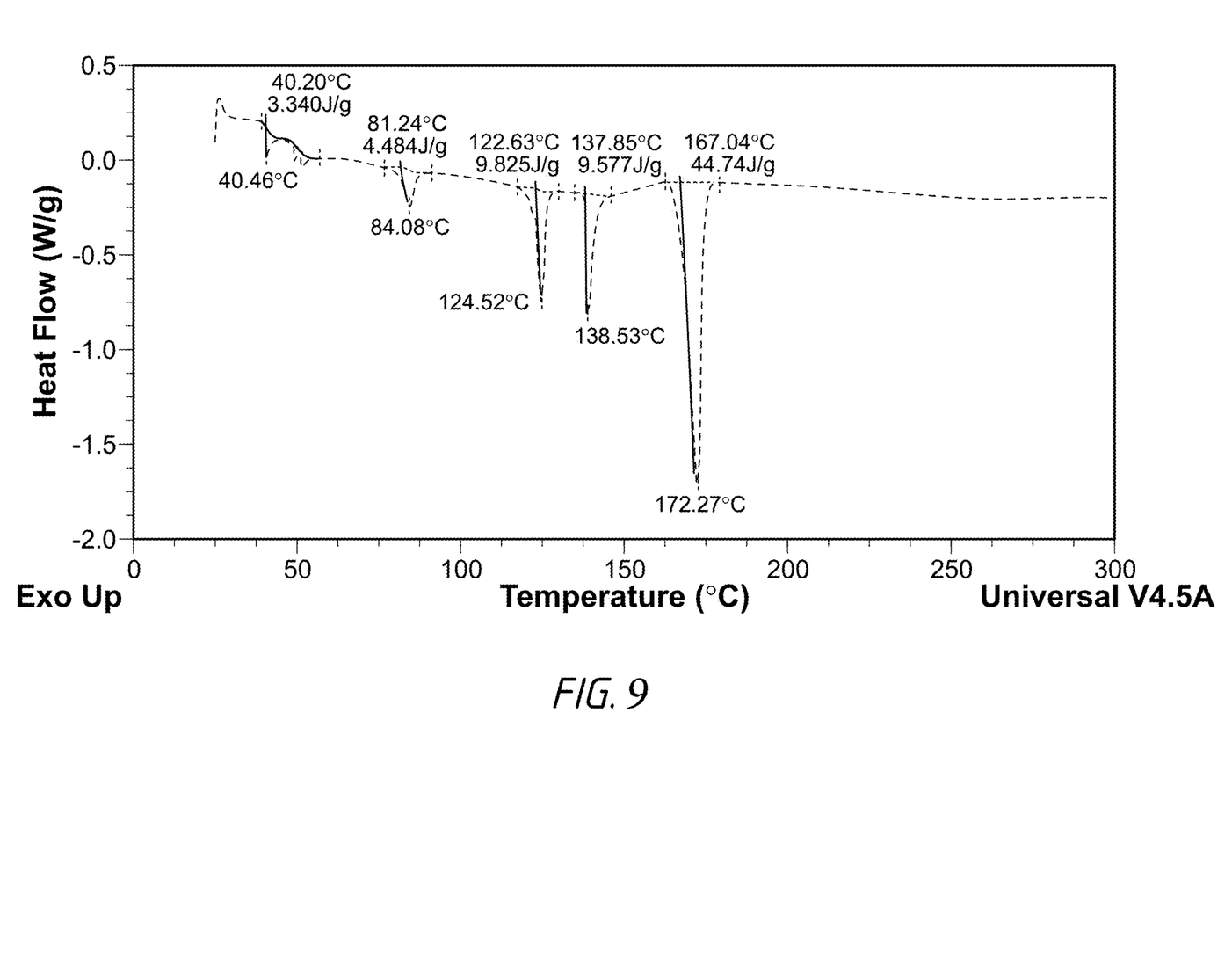
FIG. 9 is directed to DSC plot of solid-state Form III of hydrate of ABC.

A DSC plot (FIG. 9) of Form III of hydrate of ABC shows multiple endotherms (40.5, 84.1, 124.5 and 138.5° C.) prior to a melt at 172° C.

The above description is presented to enable a person of ordinary skill in the art to make and use the various embodiments. Descriptions of specific devices, techniques, and applications are provided only as examples. Various modifications to the examples described hereinafter will be readily apparent to those of ordinary skill in the art, and the general principles described herein—above and after, may be applied to other examples and applications without departing from the scope of the present invention. Thus, the various embodiments are not intended to be limited to the examples described herein after.

While the present invention has been described in terms of its specific embodiments, certain modifications and equivalents will be apparent to those skilled in the art and are intended to be included within the scope of the present invention.

The invention claimed is:

1. A compound which is crystalline Form II of anhydrous abemaciclib.

2. The compound of claim 1 having at least 2 or more X-ray powder diffraction peaks selected from 5.1, 6.2 and 16.8° 2Θ measured by CuKα radiation +/−0.2Θ.

3. The compound of claim 1 having a TGA plot showing onset of decomposition at about 320° C.

4. The compound of claim 1 having a thermal event at about 180-182° C.

5. A process for the preparation of solid-state Form II of anhydrous abemaciclib, comprising:
 (a) vacuum drying Form I of variable methanol solvate of abemaciclib at an elevated temperature for about 8 hours or more to yield solid-state Form II of anhydrous abemaciclib.

* * * * *